United States Patent [19]

Lissant

[11]  4,396,417

[45]  * Aug. 2, 1983

[54] NON-NEWTONIAN AGRICULTURAL FORMULATIONS

[75] Inventor: Kenneth J. Lissant, St. Louis, Mo.

[73] Assignee: Petrolite Corporation, St. Louis, Mo.

[ * ] Notice: The portion of the term of this patent subsequent to Aug. 9, 1994, has been disclaimed.

[21] Appl. No.: 900,207

[22] Filed: Apr. 26, 1978

Related U.S. Application Data

[63] Continuation of Ser. No. 670,681, Mar. 27, 1976, abandoned, which is a continuation of Ser. No. 871,974, Oct. 28, 1969, abandoned.

[51] Int. Cl.$^3$ ...................... A01N 55/02; A01N 61/02
[52] U.S. Cl. ........................................... 71/97; 71/65; 71/79; 71/69; 71/DIG. 1; 71/168; 71/170; 71/352; 71/354; 71/243; 71/285; 71/315.01
[58] Field of Search .......... 71/65, 97, 79, 69, DIG. 1; 424/168

[56] References Cited

U.S. PATENT DOCUMENTS

| | | | |
|---|---|---|---|
| 2,678,265 | 5/1954 | Schwerdle | 71/97 |
| 2,726,150 | 12/1955 | Wolter | 71/DIG. 1 |
| 3,190,740 | 6/1965 | Wolter | 71/DIG. 1 |
| 3,422,013 | 1/1969 | Scher | 71/DIG. 1 |
| 3,479,176 | 11/1969 | Wilson | 424/168 |
| 3,558,302 | 1/1971 | Salvesen | 71/97 |
| 3,776,857 | 12/1973 | Lindner | 71/DIG. 1 |
| 4,040,857 | 8/1977 | Lissant | 424/168 |

FOREIGN PATENT DOCUMENTS

| | | | |
|---|---|---|---|
| 815510 | 6/1959 | United Kingdom | 71/DIG. 1 |
| 851250 | 10/1960 | United Kingdom | 71/DIG. 1 |
| 1063714 | 3/1967 | United Kingdom | 71/DIG. 1 |

Primary Examiner—Glennon H. Hollrah
Attorney, Agent, or Firm—Sidney B. Ring; Hyman F. Glass; Leon J. Bercovitz

[57] ABSTRACT

Thixotropic high internal phase ratio emulsions containing biologically active agents including biocides, insecticides, fungicides, herbicides, defoliants, desiccants, seed disinfectants, growth regulators, etc., which are useful, for example, in agricultural applications. These emulsions include oily in non-oily and non-oily in oily emulsions having an internal phase of at least 60% but preferably 80-95%.

10 Claims, No Drawings

NON-NEWTONIAN AGRICULTURAL FORMULATIONS

This application is a Continuation of application Ser. No. 670,681, filed Mar. 27, 1976, now abandoned, which is a Continuation of application Ser. No. 871,974, filed Oct. 28, 1969, now abandoned.

With many biologically active materials such as agricultural and insecticidal chemicals, methods of handling and applying these materials are very important in maximizing effectiveness and minimizing deleterious side effects. For example, many agricultural chemicals and insecticides are solids or liquids which are water insoluble and must be applied in the form of emulsions or suspensions, by dusting or in the form of sprays. Stated another way, it is not only important to apply the chemical most effectively but once applied the formulation should not only depose on the leaf or plant surface but stick and spread over the surfaces so that its effectiveness is maximized.

I have now discovered that biologically active materials such as agricultural chemicals including biocides, insecticides, fungicides, herbicides, defoliants, seed disinfectants, growth regulators, etc., can be handled and applied with great effectiveness by employing non-Newtonian formulations containing such chemicals.

Being hybrid solid-liquids, i.e. behaving as solids when at rest and as liquids when pumped, they possess the best properties of both. For example, it is possible to produce non-Newtonian emulsions which when sprayed can be readily atomized by conventional equipment but which regain their high viscosity almost instantly and therefore not only allow greater control of the spray pattern and reduced drift when sprayed by low flying aircraft but also greatly minimize the run-off from plant surfaces after being applied to the plant.

These non-Newtonian agricultural preparations are best exemplified by stable high internal phase ratio emulsions. High internal phase ratio emulsions possess radically different properties from those of the low or medium internal phase ratio types. Specifically, they are non-Newtonian in nature exhibiting a yield value phenomenon and a decrease in the effective viscosity with shear rate. In contrast to gels which require significant time periods to recover their body when subject to shear, high internal phase ratio emulsions recover to high viscosities almost instantaneously.

The use of high internal phase ratio emulsions of the present invention presents many advantages in agricultural formulations. Finely divided solids or, indeed, coarse solids may be dispersed in the internal phase of a high internal phase ratio emulsion and thereby are suspended stably for extended periods of time. It is thus possible to take formulations which normally require either thickening agents to keep the solids suspended or vigorous agitation just prior to application and convert them to stable, non-settling formulations without the incorporation of large amounts of immiscible material. For instance, a water-based formulation containing solids may be formulated into a water-in-oil high internal phase ratio emulsion employing approximately 2% by volume of an oily external phase to produce a formulation possessing all the advantages of the original material but being non-settling in character.

Since high internal phase ratio emulsions are already super-creamed, they do not tend to separate on storage and therefore exhibit superior stability without the necessity of producing extremely fine particle size.

Because of the inherent high viscosity of the high internal phase ratio emulsion formulations may be produced which possess the desired viscosity properties without the incorporation of film-forming thickeners, or gelling agents. These formulations spread well but do not leave behind a sticky or adherent solid film upon the evaporation or absorption of the liquid ingredients.

Many agricultural chemicals at the present time must be applied in very small amounts. Where the active ingredient is soluble in either water or an acceptable oily phase, this can be done by preparing dilute solutions. However, by using a concentrated solution as the external phase an immiscible liquid may be used as a diluent.

Agricultural formulations may be prepared of either the oil-in-water or water-in-oil type. Aqueous solutions of materials may be incorporated as the internal phase in a high internal phase ratio water-in-oil emulsion. Similarly, oily compositions may be used as the internal phase of an oil-in-water emulsion.

By "non-Newtonian" I mean a fluid of thixotropic or pseudo-plastic character. By definition, these fluids possess the property of exhibiting variable apparent viscosity when the shear rate is varied. Stated another way, when these fluids are pumped at low shear rates, they behave as though they are extremely viscous fluids; but as the pumping rate is increased and concomitantly the shear rate increases, the fluids appear to "shear thin" and then behave as though they have low viscosities.

I have particularly found, however, that the use of emulsions, and specifically high-internal-phase-ratio emulsions, i.e. where the internal phase is a major part of the emulsion, are particularly well suited for this purpose, since from an economic standpoint, large volumes of emulsion may be formulated with inexpensive major constituents thereby providing inexpensive fluids.

The non-Newtonian fluids employed in the practice of this invention, however, are characterized by the fact that when at rest or under low shear conditions they behave like elastic solids or extremely viscous liquids; but when subjected to moderate shear rates, such as are encountered in pumping through pipes at practical, but not extremely rapid rates, the fluids behave as though they were low viscosity media. These emulsions contain an internal phase which is the major part of the emulsions; for example, at least about 60%, such as at least about 80%, but preferably in excess of about 90%, by volume, and often 95% or higher.

High internal phase emulsions of the type which can be employed in this invention are those disclosed in the following patent applications:

| Serial No. | Filed | Title | Issued Pat. No. |
|---|---|---|---|
| 411,103 | Nov. 13, 1964 | Emulsion Preparation | |
| 541,738 | Apr. 11, 1966 | Treating Thixotropic Emulsions | 3,378,418 |
| 547,581 | May 4, 1966 | Hybrid Fuels I | 3,352,109 |
| 565,702 | July 18, 1966 | Improved Thixotropic Emulsions | 3,490,237 |
| 599,332 | Oct. 19, 1966 | Stable Emulsions | |
| 637,332 | May 10, 1967 | Essentially Non-aqueous Emulsions | 3,539,406 |

Ser. No. 411,103 was abandoned in favor of continuation-in-part application Ser. No. 753,340, now U.S. Pat. No. 3,565,817. Ser. No. 599,332 is now abandoned.

The thixotropic emulsions of this invention, which have the characteristics of solids at rest and liquids when force is exerted on them, have the following advantages:

1. Yield Value—Yield values of 100 dy/cm$^2$ to more than 5,000 dy/cm$^2$ can be obtained. However, under low shear, they will flow with a viscosity approaching that of the liquid phases. On removal of shear, the recovery to original elastic solid form is nearly instantaneous. The hysteresis loop is very small.

2. Temperature Stability—Increased temperature has little effect on viscosity until the critical stability temperature is reached at which point the emulsion breaks into its liquid components. This permits a wide temperature range of use.

3. Shear Stability—Emulsions may be subjected repeatedly to shear without degradation so long as the critical shear point is not reached. At this point the emulsion breaks. However, the critical shear point is sufficiently high to permit high shear.

4. Quality Control—With these emulsions it is easy to reproduce batches with identical properties due to the absence of any "gel" structure.

5. Solids Content—Emulsions will flow well even with high solids content since they have a broad range between yield value and viscosity under modest shear.

In contrast to very high volume percent solid loading in gels or slurries which result in a "putty", these emulsions can suspend such solids in the internal phase while allowing the external phase to govern "flowability".

The above patent applications, which are by reference incorporated into the present application, relate to stable, viscous thixotropic emulsions and to the uses, preparation, etc., of these emulsions.

Whether an oil external or an aqueous external phase is employed in preparing these emulsions will depend on the particular system in which it is employed.

Thus, the emulsions employed in this invention include:

(1) Oil-in-water emulsions
(2) Water-in-oil emulsions
(3) The above emulsions of (1) and (2) where waterlike substances are employed in place of water as described in Ser. No. 637,332 filed May 10, 1967.
(4) Emulsions may be prepared by a continuous method, as described in Ser. No. 411,103, filed Nov. 13, 1964. Thus, any of the oily and non-oily materials, emulsifiers and techniques, etc. described in the above applications can be employed in preparing the emulsions of this invention.

Since these emulsions have been described in such great detail in the above applications, repetition herein is unnecessary.

The following examples are presented for purposes of illustration and not of limitation. Oxyalkylations were carried out by the general procedure described in U.S. Pat. No.2,672,886, Example 1a, columns 9 and 10.

EMULSIFIER A

An emulsifier was prepared by oxyalkylating 1,3-butanediol with 3.0 parts by weight of butylene oxide, 32.2 parts of propylene oxide and 16.6 parts of ethylene oxide in the order given.

EMULSIFIER B

An emulsifier was prepared by oxyalkylating triethyleneglycol with 5.1 parts by weight of butylene oxide, 30.0 parts of propylene oxide and 22 parts of ethylene oxide in the order given.

EMULSIFIER C

An emulsifier was prepared by oxyalkylating octyl phenol with 0.69 parts by weight of ethylene oxide.

In addition non-oxyalkylated emulsifiers can also be employed.

The following Examples illustrates the preparation of a thixotropic water external-oil high internal phase emulsion. These emulsions may be employed as the base emulsion in which the agricultural or insecticidal agent may be dissolved or dispersed.

EXAMPLE 1

Three quarts of water and 150 ml. of Emulsifier A were thoroughly mixed. One gallon of mineral oil was then added and mixed into this material until a smooth emulsion was formed. This premix was then placed into a 20 gallon open mixing vessel, equipped with an anchor type stirrer. With the stirrer revolving at about 200 rpm, additional mineral oil was added until a total of ten gallons of mineral oil had been mixed in. The result was a white, highly thixotropic, oil-in-water emulsion.

The following example illustrates the preparation of a thixotropic water external-oil high internal phase emulsion.

EXAMPLE 2

A two inch diameter, Viking pump, driven by an electric motor at 805 rpm, was equipped with an eight foot flexible hose on the outlet and a similar flexible hose on the inlet. The ends of the two hoses were placed in a 50 gallon, open head, steel drum. With this arrangement, material could be pumped out of the drum, through the pump, and back into the drum.

One gallon of water and one pint of Emulsifier B were mixed together and placed in the steel drum. While this material was circulated by the pump, mineral oil was slowly added to the intake of the pump. In about 15 minutes, 50 gallons of mineral oil had been added and the result was a thick, white, jelly-like emulsion.

The following example illustrates the preparation of an oil external-high internal water phase thixotropic emulsion.

EXAMPLE 3

A two inch diameter, Viking pump, driven by an electric motor at 850 rpm, was equipped with an eight foot flexible hose on the outlet and a similar flexible hose on the inlet. The ends of the two hoses were placed in a 50 gallon, open head, steel drum. With this arrangement, material could be pumped out of the drum, through the pump, and back into the drum.

One gallon of mineral oil and one pint of emulsifier C were mixed together and placed in the steel drum. While this material was circulated by the pump, water was slowly added to the intake of the pump. In about 15 minutes, 50 gallons of water had been added and the result was a thick, white, jelly-like emulsion.

EXAMPLE 4

Small laboratory batches of emulsions may be made in a kitchen-type mixer such as the Model C3 Kitchen Aid Mixer manufactured by the Hobart Manufacturing Company. This mixer uses a two quart glass mixing bowl and a wire beater with a planetary motion. A typical water-in-oil high internal phase ratio base emulsion was made as follows:

EXAMPLE 5

8 ml. of light mineral oil, 1 ml. of the emulsifier described in Example 1 of our copending patent applications Ser. No. 286,877 and 1 ml. of the emulsifier of Example 21 of U.S. Pat. No. 3,352,109 were placed in the mixer bowl of the Kitchen Aid Mixer. With the mixer speed set at #3, 5 ml. increments of water were added mixing thoroughly between additions, until a total of 50 ml. of water had been added. Additional water was then added slowly until a total of 190 ml. of water had been added. The result was a thick, creamy, white stable emulsion containing 95 volumes of water emulsified in 5 volumes of the oily external phase. An emulsion of this type will function as a base for a variety of formulations. For instance, an appropriate amount of phytotoxicant such as pentachlorphenol may be added to produce a defoliant. Alternatively, an insecticide such as DDT or Chlordane may be added. Other ingredients may be incorporated to suit particular purposes. When a particular active ingredient is to be incorporated into the oily phase it may be necessary to modify the emulsifier combination to obtain optimum properties. Techniques for selection of emulsifiers are described in our copending applications. If desired, suitable pigments may be dispersed in the aqueous phase.

EXAMPLE 6

17.5 ml. of kerosine and 7.5 ml. of an emulsifier mixture composed of 40 volumes of Emulsifier D, 40 volumes of Emulsifier E, and 20 volumes of Emulsifier F were thorougly mixed and placed in the bowl of the Kitchen Aid Mixer Model 4C. With the mixer speed set at $\approx 1.6$, 100 ml. of disodium methyl arsonate was added slowly while stirring. At this time a smooth, velvety emulsion had formed. The mixer speed was then increased to $\approx 3$ and more disodium methyl arsonate was added until a total of 475 ml. had been added. The result was a thick, creamy, white, stable emulsion containing 95 volumes of disodium methyl arsonate emulsified in 5 volumes of the oily external phase.

EMULSIFIER D

An emulsifier was prepared by oxyethylating nonyl phenol with 0.8 parts by weight ethylene oxide. The resulting oxyalkylate was subsequently sulfated with sulfamic acid.

EMULSIFIER E

An emulsifier was prepared by oxyethylating nonyl phenol with 1.17 parts by weight ethylene oxide.

EMULSIFIER F

An emulsifier was prepared by oxyethylating nonyl phenol with 0.599 parts by weight ethylene oxide.

As is quite evident, a wide variety of thixotropic emulsions are useful in this invention. It is, therefore, not only impossible to attempt a comprehensive catalogue of such compositions, but to attempt to describe the invention in its broadest aspects in terms of specific chemical names for the components of such emulsions would be too voluminous and unnecessary since one skilled in the art could by following the description of the invention herein prepare an appropriate emulsion. This invention encompasses the use of thixotropic and other pseudo plastic fluids in agricultural formulations and the individual components of such fluids are important only in the sense that they affect this function. To precisely define each specific useful phase of the emulsion and emulsifier in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific phases of the emulsions and emulsifiers suitable for this invention by applying them in the process set forth herein. In analogy to the case of a machine, wherein the use of certain materials of construction or dimensions of parts would lead to no practical useful result, various materials will be rejected as inapplicable where others would be operative. I can obviously assume that no one will wish to use a useless emulsion nor will be misled because it is possible to misapply the teachings of the present disclosure to do so. Thus, any thixotropic emulsion that can perform the function stated herein can be employed. Analogously other thixotropic or pseudoplastic fluids besides emulsions can be employed.

To specifically enumerate all of the materials whose application could be advantageously undertaken by the methods of this application would be impractical and unnecessarily lengthy. Materials with activity for agricultural applications may be classified in a number of ways, however, one simple classification follows. It is patterned somewhat after the method used by the U.S. Department of Agricultural, Register of Agricultural Materials.

1. Herbicides—By this, is meant a material which, when applied either to the ground or the growing plant, will significantly retard or prevent the growth of a particular type of plant life.

2. Defoliants—By this term, is meant materials which, when applied to growing plants, cause the foliage to be dropped, preferably without resulting in the complete death of the plant although in some cases, herbicidal activity is achieved by the expedient of producing complete defoliation.

3. Desiccants—By this, is meant a material which results in the drying up of the plant tissue. This may be produced by modification of the osmotic environment or by interference with normal plant growth mechanisms. In many instances it results in the loss of foliage and is sometimes similar in action to defoliation.

4. Plant Regulators—These materials are specific chemical substances which when applied to plants modify the normal growth behavior or growth habit. For instance, they may result in lengthening the internode distances as is the case with certain gibberellic acids, they may result in the retention of blossoms or fruit, in modification of the ripening time of the fruit, and so forth.

5. Insecticides—By this is meant materials which are toxic to and cause the death of insects. They are obviously employed in agriculture to control insects which would otherwise damage crops.

6. Fungicide—This material is used for the control of fungus infestation on economic plants.

7. Nematocides—This material is used to control nematode infestations.

Specified examples of materials that may be employed for some or all of the above purposes and may be found in a list published by the U.S. Department of Agricultural entitled "Summary of Registered Agricultural Pesticide Chemical Uses" (3d Edition, Mar.31, 1969) Volume 1 of this list enumerates several hundred herbicides, defoliants, desiccants and plant regulators. Volume II specifically enumerates a large number of fungicides and mematocides. Volume III lists insecticides, repellents and acaricides. These are by reference incorporated into this specification as if part hereof.

Besides materials normally classified as toxicants, certain soil modifiers and plant foods may also advantageously be applied by the methods envisioned in this patent. For instance, a solution of ammonia in water or ammonium nitrate in water which is normally furnished as a plant fertilizer may be employed as the internal phase of an HIPR water-in-oil emulsion. Suitable oil-soluble plant growth regulators or insecticides may be dissolved in the oily external phase thus allowing one to treat the field with a toxicant and a fertilizer in one application. Other combination treatments will be similarly obvious.

I claim:

1. A biologically active thixotropic high internal phase ratio emulsion useful in agricultural applications selected from the group consisting of
   (A) an oil-in-non-oil emulsion comprising an emulsifiable oil, an emulsifying agent, and an emulsifiable non-oil, said oil being present in said emulsion in an amount of at least 60% oil by volume of the emulsion, and
   (B) a non-oil-in-oil emulsion comprising an emulsifiable oil, an emulsifying agent and an emulsifiable non-oil,
said non-oil being present in said emulsion in an amount of at least 60% non-oil by volume of the emulsion, said high internal phase ratio emulsion containing a biologically effective amount of an agent useful in agricultural applications selected from the group consisting of biocides, insecticides, fungicides, herbicides, defoliants, seed disinfectants and growth regulators, said emulsion having the characteristics of an elastic solid when at rest, of an extremely viscous liquid under low shear conditions and of a low viscosity medium under moderate shear rates, said emulsion being free of any dispersant other than the emulsifying agent, and further being free of any film-forming thickeners and gelling agents, said emulsion being capable of being atomized and sprayed without any further dilution to a lower viscosity, said emulsion having the additional characteristic of being capable of spreading well but not leaving behind a sticky or adherent solid film upon evaporation or absorption of the liquid ingredients.

2. A process of applying a biologically active high internal phase ratio emulsion of claim 1 to agricultural ground or to plants growing thereon, comprising atomizing said emulsion to form a spray and contacting said ground or plants with said sprays.

3. The process of claim 2 wherein the oil in said emulsion (A) is present in an amount of at least 80% by volume of said emulsion (A) and the non-oil in said emulsion (B) is present in an amount of at least 80% by volume of said emulsion (B).

4. The process of claim 2 wherein the oil in said emulsion (A) is present in an amount of at least 90% by volume of said emulsion (A) and the non-oil in said emulsion (B) is present in an amount of at least 90% by volume of said emulsion (B).

5. The process of claim 2 wherein the oil in said emulsion (A) is present in an amount of at least 95% by volume of said emulsion (A) and the non-oil in said emulsion (B) is present in an amount of at least 95% by volume of said emulsion (B).

6. The process of claim 2 wherein said emulsion is emulsion (B) and the agent useful in agricultural applications is disodium methyl arsonate.

7. The emulsion of claim 1 where the oil in (A) is present in said emulsion (A) in an amount of at least 80% by volume of said emulsion (A) and the non-oil in (B) is present in said emulsion (B) in an amount of at least 80% by volume of the emulsion (B).

8. The emulsion of claim 7 where the oil in (A) is present in said emulsion (A) in an amount of at least 90% by volume of the emulsion (A) and the non-oil in (B) is present in said emulsion (B) in an amount of at least 90% by volume of the emulsion (B).

9. The emulsion of claim 8 where the oil in (A) is present in said emulsion (A) in an amount of at least 95% by volume of the emulsion (A) and the non-oil in (B) is present in said emulsion (B) in an amount of at least 95% by volume of the emulsion (B).

10. The emulsion of claim 9 where the emulsion is emulsion (B) and the non-oil is water and the agent useful in agricultural applications is disodium methyl arsonate.

* * * * *